(12) United States Patent
Antignani et al.

(10) Patent No.: US 6,506,573 B2
(45) Date of Patent: Jan. 14, 2003

(54) ADDITIVE FORMULATION AND METHOD OF USE THEREOF

(75) Inventors: Antoinette F. Antignani, Chatham, NJ (US); Emy Cheng, Wayne, NJ (US); Jeffrey M. Evans, Broken Bow, NE (US); Nicholas A. Grippi, Ramsey, NJ (US); Bryan S. Wong, South Plainfield, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/180,396

(22) Filed: Jun. 26, 2002

(65) Prior Publication Data

US 2002/0192734 A1 Dec. 19, 2002

Related U.S. Application Data

(63) Continuation of application No. 09/755,269, filed on Jan. 5, 2001, now abandoned, which is a continuation of application No. 09/304,382, filed on May 4, 1999, now Pat. No. 6,187,553, which is a continuation of application No. 08/923,838, filed on Sep. 4, 1997, now abandoned.

(51) Int. Cl.[7] .............................................. C12Q 001/34
(52) U.S. Cl. ...................................................... 435/18
(58) Field of Search ............................... 435/18, 289.1, 435/13, 177, 269

(56) References Cited

U.S. PATENT DOCUMENTS 6,187,553 B1 * 2/2001 Antignani et al. ............. 435/13

* cited by examiner

*Primary Examiner*—Louise N. Leary
(74) *Attorney, Agent, or Firm*—Scott J. Rittman, Esq.; Nanette S. Thomas, Esq.

(57) ABSTRACT

An additive formulation comprising heparinase and trehalose, a method for using the formulation and a device containing the formulation. The additive formulation is useful in substantially neutralizing residual heparin from a blood sample when used in a blood collection tube without interfering with the clinical analysis of the blood sample.

4 Claims, 1 Drawing Sheet

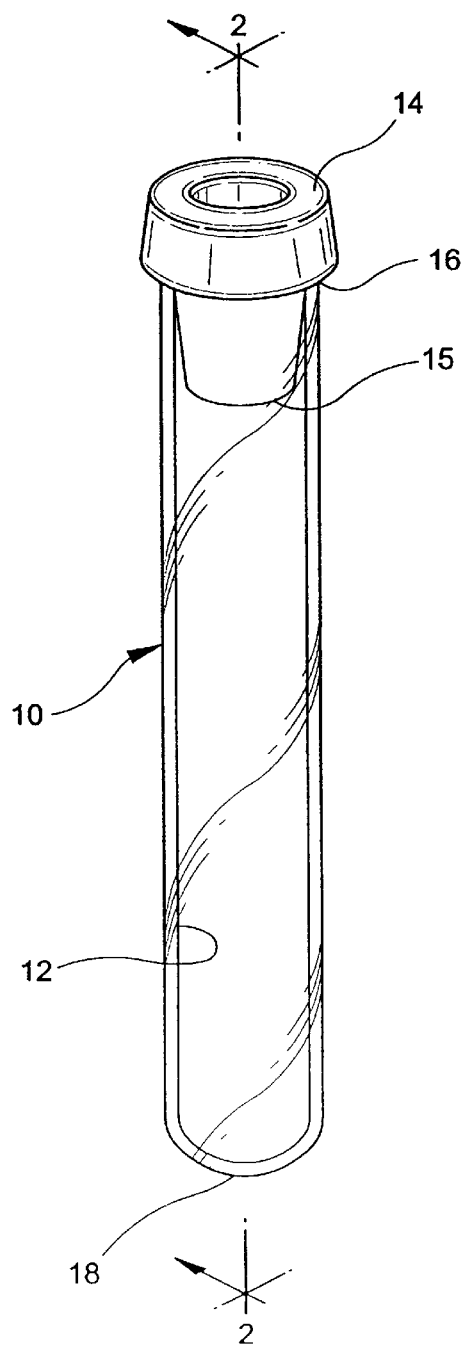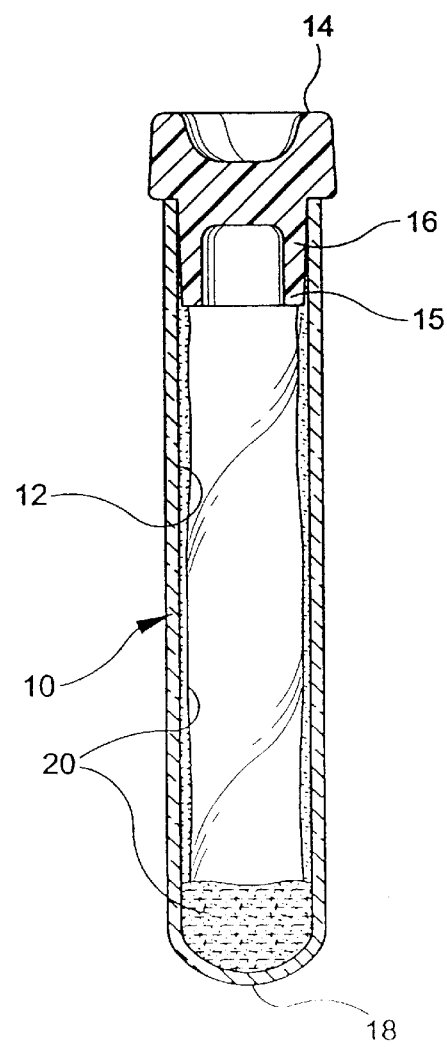

US 6,506,573 B2

ADDITIVE FORMULATION AND METHOD OF USE THEREOF

This application is a continuation of patent application Ser. No. 08/923,838 filed Sep. 4, 1997, now abandoned, which was a continuation of Ser. No. 09/304,382 filed May 4, 1999, now U.S. Pat. No. 6,187,553, which was a continuation of Ser. No. 09/755,269 filed Jan. 5, 2001, now abandoned.

BACKGROUND OF THE INVENTION

1. Field of the Invention

This invention relates to an additive preparation, the method of making the additive preparation and the method of using the additive preparation. The additive preparation is most particularly for use in blood collection devices wherein the additive preparation comes in contact with a blood specimen that has been previously treated with heparin. The additive preparation desirably comprises a formulation comprising heparinase and a carbohydrate. The additive formulation is desirably spray dried onto the inner wall of a blood collection device. In particular, the additive formulation of the present invention exhibits stability even when subjected to gamma irradiation.

2. Description of Related Art

Heparin is an anticoagulant that is used in surgical procedures and dialysis therapy to prevent clotting in intravenous lines and in the treatment of thrombolytic disorders. It affects thrombin activity by catalyzing the action of anti-thrombin III (ATIII), thereby preventing the conversion of fibrinogen to fibrin which results in clotting inhibition.

Heparin is also applied to a variety of clinical situations in addition to its use as an anticoagulant. It is used in hemodialysis treatments to prevent the blood from clotting during dialysis and as an antithrombotic agent in the treatment of deep venous thrombosis and orthopedic surgery. As a prophylactic of thrombosis, it is used in conjunction with prolonged intermittent intravenous administration of drugs and fluids. Recently, heparin also has been used in fibrinolytic therapy where it is co-administered with promoters of fibrin degradation such as tissue plasminogen activator, streptokinase or urokinase. Therefore, varying quantities of heparin are found in the blood of numerous hospitalized patients.

Patients receiving heparin therapy or who have been exposed to heparin through intravenous lines are frequently tested by a variety of means for the assessment of their hematological status, to monitor heparin therapy itself or for biochemical assays. However, the presence of heparin in blood specimens collected from heparinized patients causes several problems because the heparin interferes with clotting thereby rendering the results ambiguous or unobtainable. For biochemical assays, such problems include the prolongation of clotting and insufficient removal of fibrin thereby resulting in continual and unpredictable clot formation in specimens without added anticoagulants.

Furthermore, specimens with identifiable extended clotting times require additional handling and longer preparation times to remove or manage the heparin interference. In addition, if clots are not identified prior to assaying the specimen on an automated analyzer, clots forming within the instrument may lead to incomplete test results and/or instrument clogging. Therefore, testing accuracy is minimized, unnecessary instrument downtime may need to take place to unclog the instrument, additional specimens may need to be obtained to repeat the test and technical operator time is increased.

It is therefore desirable to resolve the heparin interference problem with a method that could expeditiously and specifically remove heparin from blood samples immediately after blood collection. The additive needed to accomplish this must function over a broad range of conditions. Such conditions include, but are not limited to, heparin being neutralized, quickly, while the additive itself, should not impart any effects on blood components over a lengthy exposure period. Furthermore, the treated samples containing heparin should give a result identical to untreated samples that have not been exposed to heparin.

Therefore, with the increasing demand for reducing turn around time and for fibrin free serum specimens there is a need to remove residual heparin from specimens collected from heparinized patients.

SUMMARY OF THE INVENTION

The present invention is a gamma irradiation stable additive formulation comprising a degradative glucanase enzyme specific for heparin and a stabilizer. The formulation may be effectively used as an additive in a tube to neutralize residual heparin in specimens taken from heparinized patients and accelerate clotting. In addition, the formulation is irradiation stable. The additive formulation is useful in effectively minimizing interference from heparin in a blood sample when used in a blood collection tube without interfering with the clinical analysis.

The additive formulation desirably comprises a degradative glucanase enzyme specific for heparin such as heparinase.

Desirably, the stabilizer of the additive formulation is to provide heparinase stability during controlled drying and elevated temperature storage of the formulation so that the heparinase can be stable.

The additive formulation preferably comprises heparinase and a disaccharide. Most preferably, the additive formulation comprises heparinase and trehalose.

An effective additive formulation compromising heparinase and trehalose, may be sprayed onto the wall of a tube and be rendered irradiation stable in the tube by controlled drying and prior removal of oxygen in the tube by back-flushing with an alternate gas.

The additive formulation may further comprise a buffer solution so that the formulation resists changes in pH.

Most preferably, the additive formulation comprises:
(a) from about 50 IU/mL to about 80 IU/mL of degradative glucanase enzyme specific for heparin;
(b) from about 8 to about 12 weight percent of a stabilizer; and
(c) about 15 mL of a 150 millimolar (mM) buffer.

The unit heparinase is an International Unit (IU) which is the amount of heparinase which causes 1 micromole of double bonds to form per minute based on a molar extinction coefficient of about 5.1 at about 232 nm for the degradation products, the unsaturated uronic acids.

Most preferably, the additive formulation is used in a collection device such as a blood collection tube wherein the formulation is spray-dried onto the interior of the tube.

Additive formulations of the present invention are useful in providing neutralization of heparin and clotting of blood specimens.

Another attribute of the additive formulation is that it is stable when heated, dried and irradiated.

Advantages of the additive is that it achieves heparin neutralization of a blood sample of a heparinized patient faster and more completely than other available methods. Therefore, the additive formulation is useful in substantially removing heparin from a blood sample when used in a blood collection tube without interfering with the clinical analysis. The combination of the heparinase and trehalose in proper proportion is useful in eliminating the interference in clotting due to the presence of heparin. Therefore the additive formulation will help to deactivate residual heparin in specimens collected from heparinized patients. This method would reduce the handling of specimens from heparinized patients whereby current handling requires manual removal of latent fibrin from slow clotting specimens. Therefore, the method obviates the requirement for identifying problematic specimens or patient populations.

An advantage of the additive formulation comprising heparinase and trehalose and oxygen removal is a unique heat and radiation stable formulation. The formulation provides substantial recovery of about 50% to about 60% post irradiation.

An important attribute of the formulation of the present invention is that it exhibits stability even when subjected to gamma irradiation.

A method of protecting heparinase against denaturation during drying and irradiation, comprises the steps of incorporating an effective amount of trehalose into the heparinase. Therefore, according to the present invention there is provided a method of drying heparinase at a temperature above ambient, by incorporating trehalose into the heparinase which is to be spray dried, followed by oxygen removal prior to irradiation by back flushing the tube with a gaseous mixture of $CO_2/H_2$; 80:20 ratio.

DESCRIPTION OF THE DRAWINGS

FIG. 1 is a perspective view of a typical blood collection tube with a stopper.

FIG. 2 is a longitudinal sectional view of the tube of FIG. 1, taken along line 2—2, comprising the spray dried additive formulation of the present invention.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The additive formulation preferably comprises:
(a) heparinase; and
(b) trehalose.

Heparinase is a composition that can eliminate heparin interference of normal blood function. The heparinase present in the additive formulation of the present invention is selected to neutralize residual heparin in specimens collected from heparinized patients.

Heparinase 1 (EC 4.2.2.7) is an enzyme derived from Flavobacterium heparinum, a Gram negative non pathogenic bacteria. Heparinase cleaves heparin at 11 active sites (alpha-glycosidic linkages), including the ATIII binding site, and can deactivate heparin in a specimen allowing normal clot formation.

The preferred heparinase in the additive formulation is heparinase isolated from Flavobacterium heparinum has an optimal activity at pH of about 6.5 to about 7.0; sodium chloride concentration of about 0.1M and of about 37° C., wherein the anticoagulant component does not bind to a polysulfated resin at about pH 7.0, conductivity between about 3 and about 12 mmhos, and the heparinase does bind to a polysulfated resin at pH 7.0, conductivity between 3 and 12 mmhos. The method of preparing and using anticoagulant free heparinase is described in U.S. Pat. Nos. 5,338,677 and 5,262,325 and are incorporated herein by reference. A highly purified bacterial heparinase is available from IBEX Technologies, St. Laurent, Quebec, Canada.

Preferably, heparinase is present in the additive formulation in an amount from about 50 IU/mL to about 80 IU/mL, and most preferably at about 65 IU/mL.

A stabilizer is a component which can provide protection to enzymes and proteins by maintaining the macromolecular structure of these during drying.

Stabilizers are typically characterized by their ability to provide protection against chemical degradation during radiation and elevated temperature storage.

A specific selection of stabilizers is required for the additive formulation so that the activity of heparinase is maintained post heating, drying and/or irradiation.

Classes of stabilizers that may be used in the additive formulation include but are not limited to carbohydrates.

A suitable stabilizer for the additive formulation includes, but is not limited to, trehalose, mannitol, mannose and ammonium sulfate.

Most preferably, the stabilizer in the additive formulation is trehalose.

Preferably, trehalose is present in the additive formulation in an amount from about 8 weight percent to about 12 weight percent, and most preferably at about 10 weight percent.

Trehalose, alpha-D-glucopyranosyl-alpha-D-glucopyranoside, is a naturally occurring non-reducing disaccharide which is typically associated with cell protection. It is known that some organisms, both plant and animal, can resist desiccation to very low levels of body water during drought conditions. These organisms include brine shrimps cysts (*Artemia salina*), the resurrection plant (*Selaginella lepidophylla*) and bakers yeast (*Saccharomyces cerevisiae*). They all share, as a common feature, the presence of large amounts of trehalose in their cells.

While there is no consensus view as to how trehalose exerts it protective effects on cells, one hypothesis is that it substitutes for the bound water on membrane components of the living organism and prevents denaturation due to loss of bound (structural) water. It has also been found that the effect is exhibited not only in living cells, but surprisingly also in macromolecules themselves in a purified, isolated state.

Trehalose is used in the present invention to preserve the stability of the heparinase. Heparinase can only be stored for brief time period and the stability of heparinase is diminished upon heating and irradiation. By combining trehalose with heparinase, the stability of the heparinase is preserved when heated and/or dried and by removal of oxygen the stability is further preserved when irradiated.

It is believed that trehalose preserves the structure and function of heparinase in the dry state due to hydrogen bonding of trehalose molecules via their hydroxyl groups, to appropriate groups on the macromolecule. In this way trehalose takes the place of structural (bound) water molecules so that there is no collapse of macromolecular structure upon spray drying of the formulation and later when the formulation is irradiated. The trehalose acts as a dry scaffold maintaining the structural integrity of the heparinase.

A buffer solution may also be used in the formulation of the present invention to provide an aqueous medium to the formulation that resists changes in pH.

Buffers that may be used in the formulation of the present invention include TRIS, sodium chloride and sodium phosphate. The most preferred buffer is sodium phosphate because of its pH buffering capacity.

Preferably, sodium phosphate is present in the additive formulation in an amount of about 15 mL of a 150 mM solution.

The additive formulation of the present invention is prepared for spray drying as follows:
a) measuring the activity of the heparinase;
b) adjusting the activity of the heparinase from about 50 IU/mL to about 80 IU/mL by adding a sodium phosphate buffer of about 15 mL of 150 mM to the heparinase;
c) adding from about 8 weight percent to about 12 weight percent of trehalose to the heparinase to form the additive formulation;
d) filtering the formulation through a 0.22 μM filter to remove microbial contamination; and
e) spray coating the inside of the tube (6 mL capacity) with about 10 to about 20 microliters of the filtered formulation.

Other ingredients which are conventional or desirable in various additive formulations relating to clot activators may also be added to the formulation as long as they do not adversely affect the overall properties of the additive formulation composition. Such clot activators include but are not limited to silica, thrombin, and elegic acid.

If desired, the additive formulation may also include gels and surfactants.

Most preferably, the additive formulation of the present invention may be used in blood collection devices. Most notably, in blood collection tubes. The blood collection tubes may be either an evacuated blood collection device or a non-evacuated blood collection device. The blood collection device is desirably made of plastic, such as but not limited to polyethylene terephthalate, or polypropylene, or glass.

Referring to the drawings in which like reference characters refer to like parts throughout the several views thereof, FIG. 1 shows a typical blood collection tube 10, having an open end 16, a closed end 18 and a stopper 14 that includes a lower annular portion or skirt 15 which extends into and presses against the inside wall 12 of the tube for maintaining stopper 14 in place.

FIG. 2 shows the use of the additive formulation of the present invention in a typical blood collection tube. An additive formulation 20 is shown on the inside wall of the tube.

A blood specimen sample of interest can be transferred into tube 10 that comprises the additive formulation 20, wherein the specimen contacts the additive formulation so that the formulation rapidly dissolves into the specimen and neutralizes any heparin which is present. Tube 10 is then allowed to clot, at which time it is centrifuged and the serum of the sample is ready for analysis.

The method for preparing a collection device with the additive formulation of the present invention comprises the following steps:
(a) preparing an additive formulation comprising a mixture of 150 mM sodium phosphate buffer, about 50 IU/mL to about 80 IU/mL of heparinase and about 8 weight percent to about 12 weight percent of trehalose at a pH from about 6.95 to about 7.05;
(b) filtering the formulation through a 0.22 μM filter;
(c) applying about 10 to about 20 microliters of the additive formulation to the inner wall surface of a collection device with a means that produces a fine mist of the formulation;
(d) drying the applied formulation by applying an air jet or forced air to the inner wall of the coated device from about 25 to about 30° C. for a period from about 5 to about 10 minutes;
(e) vacuum drying the collection device for about 2 hours at about 35° C. at about 600 millimeters of mercury (Hg);
(f) removing oxygen from the device by back flushing the device with a gaseous mixture of $CO_2/H_2$ (80/20);
(g) stoppering the device; and
(h) irradiating the device with the formulation by gamma irradiation within 2 to 5 hours of step (g) at about 1.5 M rads.

It is preferable that the additive formulation is metered and dispensed into the collection device, such as a blood collection tube, by a volumetric type device, such as a positive displacement pump. The formulation concentration (amount of heparinase and trehalose per unit volume of formulation) is tailored with the dispense volume so that the desired amount of formulation is dispensed into the device. Other spraying techniques include ultrasonic spraying.

The additive formulation of the present invention may be used to eliminate the physiological effects of heparin on blood components in a mixture of blood components and heparin in a blood collection tube comprising the following method:
(a) preparing an additive formulation comprising heparinase, trehalose; and a buffer;
(b) spray coating the additive formulation inside a blood collection tube;
(c) drying the applied formulation by applying an airjet or forced air to the inner wall of the coated tube from about 25 to 30° C. from about 5 to about 10 minutes;
(d) vacuum drying the applied formulation for about 2 hours;
(e) removing the oxygen from the tube by back flushing the tube with a gaseous mixture of $CO_2/H_2$ (80/20);
(f) stoppering the tube;
(g) irradiating the tube within 2 to 5 hours of stoppering at about 1.5 Mrads;
(h) adding a blood specimen containing heparin into the tube;
(i) mixing the specimen in the tube with the additive formulation by manual inversion from about 5 to about 10 times; and
(j) allowing the blood to clot.

The following examples are not limited to any specific embodiment of the invention, but are only exemplary.

EXAMPLE 1

Method of Making the Additive Formulation

An additive formulation was made by mixing in a suitably sized vessel, for a sufficient amount of time to ensure homogeneity, to form a formulation with the following ingredients:

TABLE 1

| Ingredients | Amounts |
| --- | --- |
| Heparinase | 50–80 IU/mL |
| Trehalose | 8–12% w/v |
| Sodium Phosphate | 150 mM |

The activity of the heparinase was first measured. Then the activity of the heparinase was adjusted from about 50 to about 80 IU/mL by the addition of about 15 mL of 150 mM of sodium phosphate.

Then from about 8 to about 12 weight percent trehalose was added to the heparinase to form the additive formulation. The formulation was then filtered through a 0.22 mM filter to remove microbial contamination.

EXAMPLE 2

Method of Preparing a Collection Device with the Additive Formulation

About fifteen (15) microliters of the formulation that was prepared in Example 1 was spray coated into each of 100 tubes (VACUTAINER Brand Plus Serum tubes, 6 mL, Catalog No. 367815, Becton, Dickinson and Company, Franklin Lakes, N.J.). Each tube was then air dried from about 25 to about 30° C. The tubes were then vacuum dried for about 2 hours at about 35° C. at about 600 millimeters Hg. After the 2 hours, the tubes were back flushed with a gaseous mixture of $CO_2/H_2$ (80/20), stoppered and irradiated within 2 to 5 hours of stoppering.

EXAMPLE 3

Stability of the Additive Formulation

The additive formulation that was made in Example 1 was tested for heat and irradiation stability. A tube containing only spray dried heparinase (no trehalose), a tube containing the formulation of the present invention as made in Examples 1 and 2, (with oxygen removal and back flushing) and a tube containing the formulation of the present invention as made in Examples 1 and 2 but without oxygen removal (no backflushing) were tested for heat stability. As reported in Table 2, the tubes were stored at 25° C. and 40° C. and then the percent recovery of heparinase was measured by activity. The results are shown in Table 2.

TABLE 2

HEPARINASE RECOVERY RESULTS
(% Heparinase Activity Recovery vs.
Calculated Application of Heparinase Activity)

| SAMPLE TREATMENT | No Trehalose | With Trehalose, No $CO_2H_2$ backflush | With Trehalose and with $CO_2/H_2$ backflush |
| --- | --- | --- | --- |
| Non-Irradiated 25° C. storage | 80% | 90% | 90% |
| Non-Irradiated 40° C. storage | 0% | 90% | no data |
| Irradiated 1.5 Mrads 25° C. storage | 0% | 0% | 50% |

As shown by the results reported in Table 2, trehalose renders temperature stability for heparinase recovery. It is believed that based upon the results reported in to Table 2 that heparinase degradation during irradiation is associated with residual moisture and/or the presence of oxygen. Therefore, heparinase degradation during irradiation can be controlled with combinations of drying and oxygen removal by backflushing of the collection container as illustrated in this Example.

EXAMPLE 4

Comparative Analysis of Clotting of Heparinized Blood with and without Heparinase An aliquot of lithium heparin treated whole blood was equally transferred into Tube #2 that did contain the additive formulation of the present invention as prepared in Examples 1 and 2 and into Tube #3 which did not contain any additive formulation. An aliquot of untreated whole blood (no heparin) was added to Tube #1 which was a control which did not contain heparin or heparinase. Each sample was evaluated to determine if the heparin in the blood sample was neutralized. Each Tube was inspected for evidence of clotting at 5 to 10 min intervals and the final clot times are shown in Table 3.

The formulation of the present invention neutralized heparin in human blood by allowing normal clot formulation to occur in 40 minutes as shown by the results reported for Tube #2. In Tube #3, which contained heparin but did not contain the formulation of the present invention, the blood sample did not clot, but remained anticoagulated by the heparin. Tube #1 without heparin or heparinase allowed the blood to clot in 15 minutes.

TABLE 3

Clotting Study of Heparinized Blood
Collected into Tubes Containing Heparinase

| Tube # | Heparinase (IU/mL) | Heparin (USP/mL) | Clot Time (min) |
| --- | --- | --- | --- |
| 1 | 0 | 0 | 15 |
| 2 | 0.5* | 24 | 40 |
| 3 | 0 | 24 | no clot |

*post irradiation at a 50% loss.

What is claimed is:

1. A container for collection of a heparin-containing blood sample, the container comprising:

an inner surface and an outer surface, and a spray-dried additive formulation on at least a portion of the inner surface, the formulation comprising heparinase, trehalose, and a buffer.

2. The container of claim 1, wherein the container is a tube.

3. The container of claim 2, wherein the tube is plastic.

4. The container of claim 2, wherein the tube is an evacuated tube.

* * * * *